United States Patent
Kurth

(10) Patent No.: US 10,159,585 B2
(45) Date of Patent: Dec. 25, 2018

(54) PROSTHETIC LINER

(71) Applicant: Ossur Iceland ehf, Reykjavik (IS)

(72) Inventor: Christof Werner Björn Kurth, Reykjavik (IS)

(73) Assignee: OSSUR ICELAND EHF, Reykjavik (IS)

( * ) Notice: Subject to any disclaimer, the term of this patent is extended or adjusted under 35 U.S.C. 154(b) by 47 days.

(21) Appl. No.: 15/494,968

(22) Filed: Apr. 24, 2017

(65) Prior Publication Data
US 2017/0304085 A1    Oct. 26, 2017

(30) Foreign Application Priority Data

Apr. 25, 2016  (EP) ..................... 16166902

(51) Int. Cl.
*A61F 2/80* (2006.01)
*A61F 2/78* (2006.01)

(52) U.S. Cl.
CPC .... *A61F 2/7812* (2013.01); *A61F 2002/7806* (2013.01); *A61F 2002/7818* (2013.01); *A61F 2002/7837* (2013.01); *A61F 2002/7887* (2013.01); *A61F 2002/802* (2013.01)

(58) Field of Classification Search
CPC ............ A61F 2/7843; A61F 2002/7818; A61F 2002/7837; A61F 2002/802; A61F 2002/805; A61F 2002/807
USPC .............................................. 623/32, 34, 36
See application file for complete search history.

(56) References Cited

U.S. PATENT DOCUMENTS

| | | | |
|---|---|---|---|
| 980,457 | A | 1/1911 | Toles |
| 1,398,824 | A | 11/1921 | Abrams |
| 1,893,853 | A | 1/1933 | Tullis |
| 2,325,656 | A | 8/1943 | Brophy |
| 2,464,443 | A | 3/1949 | Ganoe et al. |
| 2,530,285 | A | 11/1950 | Catranis |
| 2,533,404 | A | 12/1950 | Sharp et al. |

(Continued)

FOREIGN PATENT DOCUMENTS

| | | |
|---|---|---|
| AT | 369 978 B | 2/1983 |
| DE | 484 363 C | 10/1929 |

(Continued)

OTHER PUBLICATIONS

"Silicone-Only Suspension (SOS) with Socket-Loc and the Ring for the Lower Limb", found at, http://www.oandp.org/jpo/library/1995_01_002.asp. Journal of Prosthetics and Orthotics 1995;vol. 7, No. 1, p. 2.

(Continued)

*Primary Examiner* — David H Willse
(74) *Attorney, Agent, or Firm* — Workman Nydegger

(57) ABSTRACT

A prosthetic liner includes a flexible elongate, generally conical body portion formed from an elastomeric material. The body portion defines an inner surface, an outer surface forming a liner profile between a distal end and a proximal end, and an axis extending between the distal and proximal ends. At least one seal element extends circumferentially about the axis and protrudes radially outward a distance from the liner profile. The at least one seal element has a seal height defined between the liner profile and a radially outward end of the at least one seal element. The seal height varies circumferentially about the axis between a first seal height and a second seal height.

20 Claims, 5 Drawing Sheets

(56) References Cited

U.S. PATENT DOCUMENTS

| | | | |
|---|---|---|---|
| 2,634,424 A | 4/1953 | O'Gorman | |
| 2,671,225 A | 3/1954 | Schoene et al. | |
| 2,689,351 A | 9/1954 | Schindler | |
| 2,808,593 A | 10/1957 | Andersen | |
| 3,393,407 A | 7/1968 | Kandel | |
| 3,587,572 A | 6/1971 | Evans | |
| 3,671,980 A | 6/1972 | Baird | |
| 3,947,897 A | 4/1976 | Owens | |
| 4,128,903 A | 12/1978 | Marsh et al. | |
| 4,215,679 A | 8/1980 | Rustin | |
| 4,311,317 A | 1/1982 | Bartels | |
| 4,319,413 A | 3/1982 | Mattil | |
| 4,347,204 A | 8/1982 | Takagi et al. | |
| 4,474,573 A | 10/1984 | Deity | |
| 4,635,626 A | 1/1987 | Lerman | |
| 4,738,249 A | 4/1988 | Linman et al. | |
| 4,767,735 A | 8/1988 | Ewen et al. | |
| 4,885,828 A | 12/1989 | Kozlowski | |
| 4,908,037 A | 3/1990 | Ross | |
| 4,923,474 A | 5/1990 | Klasson et al. | |
| 5,007,937 A | 4/1991 | Fishman et al. | |
| 5,055,528 A | 10/1991 | Kioka et al. | |
| 5,108,456 A * | 4/1992 | Coonan, III | A61F 2/7843 623/26 |
| 5,122,583 A | 6/1992 | Ewen et al. | |
| 5,139,523 A | 8/1992 | Paton et al. | |
| 5,163,965 A | 11/1992 | Rasmusson et al. | |
| 5,169,161 A | 12/1992 | Jones | |
| 5,226,918 A | 7/1993 | Silagy et al. | |
| 5,244,716 A | 9/1993 | Thornton et al. | |
| 5,314,496 A | 5/1994 | Harris et al. | |
| 5,376,129 A | 12/1994 | Faulkner et al. | |
| 5,376,131 A | 12/1994 | Lenze et al. | |
| 5,387,245 A | 2/1995 | Fay et al. | |
| 5,549,709 A | 8/1996 | Caspers | |
| 5,571,208 A | 11/1996 | Caspers | |
| 5,571,209 A | 11/1996 | Brown, Sr. | |
| 5,593,454 A | 1/1997 | Helmy | |
| 5,658,353 A | 8/1997 | Layton | |
| 5,702,489 A | 12/1997 | Slemker | |
| 5,718,925 A | 2/1998 | Kristinsson et al. | |
| 5,728,168 A | 3/1998 | Laghi et al. | |
| 5,728,170 A | 3/1998 | Becker et al. | |
| 5,735,906 A | 4/1998 | Caspers | |
| 5,830,237 A | 11/1998 | Kania | |
| 5,885,674 A | 3/1999 | Maemoto et al. | |
| 5,888,216 A | 3/1999 | Haberman | |
| 5,888,230 A | 3/1999 | Helmy | |
| 5,904,722 A | 5/1999 | Caspers | |
| 5,931,872 A | 8/1999 | Lohmann | |
| 5,972,036 A | 10/1999 | Kristinsson et al. | |
| 5,980,577 A | 11/1999 | Radis et al. | |
| 6,076,284 A | 6/2000 | Terlizzi | |
| 6,136,039 A | 10/2000 | Kristinsson et al. | |
| 6,149,691 A | 11/2000 | Fay et al. | |
| 6,171,431 B1 | 1/2001 | Gallagher, Jr. et al. | |
| 6,231,616 B1 | 5/2001 | Helmy | |
| 6,231,617 B1 | 5/2001 | Fay | |
| 6,273,918 B1 | 8/2001 | Yuhasz et al. | |
| 6,287,345 B1 | 9/2001 | Slemker et al. | |
| 6,361,568 B1 | 3/2002 | Hoerner | |
| 6,368,357 B1 | 4/2002 | Schon et al. | |
| 6,406,499 B1 | 6/2002 | Kania | |
| 6,468,938 B1 | 10/2002 | Govoni et al. | |
| 6,485,776 B2 | 11/2002 | Janusson et al. | |
| 6,508,842 B1 | 1/2003 | Caspers | |
| 6,544,292 B1 | 4/2003 | Laghi | |
| 6,554,868 B1 | 4/2003 | Caspers | |
| 6,585,774 B2 | 7/2003 | Dean, Jr. et al. | |
| 6,626,952 B2 | 9/2003 | Janusson et al. | |
| 6,645,253 B2 | 11/2003 | Caspers | |
| 6,706,364 B2 | 3/2004 | Janusson et al. | |
| 6,726,726 B2 | 4/2004 | Caspers | |
| 6,761,742 B2 | 7/2004 | Caspers | |
| 6,852,269 B2 | 2/2005 | Eberle et al. | |
| 6,926,742 B2 | 8/2005 | Caspers et al. | |
| 6,929,125 B1 | 8/2005 | Seamans | |
| 6,964,688 B1 | 11/2005 | Kania | |
| 7,001,563 B2 | 2/2006 | Janusson et al. | |
| 7,025,793 B2 | 4/2006 | Egilsson | |
| 7,118,602 B2 | 10/2006 | Bjarnason | |
| 7,144,429 B2 | 12/2006 | Carstens | |
| 7,169,188 B2 | 1/2007 | Carstens | |
| 7,169,189 B2 | 1/2007 | Bjarnason et al. | |
| 7,235,108 B2 | 6/2007 | Carstens | |
| 7,291,182 B1 | 11/2007 | Kania | |
| 7,351,264 B2 | 4/2008 | Wilson | |
| 7,427,297 B2 | 9/2008 | Patterson et al. | |
| 7,592,286 B2 | 9/2009 | Morini et al. | |
| 7,749,281 B2 | 7/2010 | Egilsson | |
| 7,771,487 B2 | 8/2010 | Mantelmacher | |
| 7,909,884 B2 | 3/2011 | Egilsson et al. | |
| 8,034,120 B2 | 10/2011 | Egilsson et al. | |
| 8,052,760 B2 | 11/2011 | Egilsson et al. | |
| 8,097,043 B2 | 1/2012 | Egilsson | |
| 8,206,459 B1 | 6/2012 | Lock et al. | |
| 8,372,159 B2 | 2/2013 | MacKenzie | |
| 8,911,506 B2 | 12/2014 | Egilsson et al. | |
| 9,060,885 B2 | 6/2015 | Egilsson et al. | |
| 9,066,821 B2 | 6/2015 | Egilsson et al. | |
| 9,603,726 B2 | 3/2017 | Egilsson et al. | |
| 9,707,106 B2 | 7/2017 | Egilsson et al. | |
| 2001/0005798 A1 | 6/2001 | Caspers | |
| 2001/0016781 A1 | 8/2001 | Caspers | |
| 2002/0040248 A1 | 4/2002 | Karason | |
| 2002/0087215 A1 | 7/2002 | Caspers | |
| 2002/0091449 A1 | 7/2002 | Caspers et al. | |
| 2002/0099450 A1 | 7/2002 | Dean, Jr. et al. | |
| 2002/0165619 A1 | 11/2002 | Hellberg | |
| 2002/0183859 A1 | 12/2002 | Houser | |
| 2003/0181989 A1 | 9/2003 | Eberle et al. | |
| 2003/0191539 A1 | 10/2003 | Caspers | |
| 2004/0024322 A1 | 2/2004 | Caspers | |
| 2004/0030411 A1 | 2/2004 | Caspers | |
| 2004/0040248 A1 | 3/2004 | Vilnes | |
| 2004/0098136 A1 | 5/2004 | Caspers | |
| 2004/0122528 A1 | 6/2004 | Egilsson | |
| 2004/0143345 A1 | 7/2004 | Caspers | |
| 2004/0167638 A1 | 8/2004 | Caspers | |
| 2004/0181290 A1 | 9/2004 | Caspers | |
| 2004/0236434 A1 | 11/2004 | Carstens | |
| 2004/0243251 A1 | 12/2004 | Carstens | |
| 2004/0243252 A1 | 12/2004 | Carstens | |
| 2005/0101693 A1 | 5/2005 | Arbogast et al. | |
| 2005/0216095 A1 | 9/2005 | Egilsson | |
| 2005/0240282 A1 | 10/2005 | Rush et al. | |
| 2005/0240283 A1 | 10/2005 | Kania | |
| 2005/0267598 A1 | 12/2005 | Bjarnason et al. | |
| 2005/0267599 A1 | 12/2005 | Bjarnason | |
| 2006/0212128 A1 | 9/2006 | Nachbar | |
| 2006/0293762 A1 | 12/2006 | Schulman et al. | |
| 2007/0005149 A1 | 1/2007 | Egilsson et al. | |
| 2007/0021295 A1 | 1/2007 | Morini et al. | |
| 2007/0027556 A1 | 2/2007 | Wilson | |
| 2007/0043450 A1 | 2/2007 | Pickering et al. | |
| 2007/0061017 A1 | 3/2007 | Wilson | |
| 2007/0123998 A1 | 5/2007 | Egilsson et al. | |
| 2007/0179606 A1 | 8/2007 | Huyghe et al. | |
| 2008/0089218 A1 | 4/2008 | Egilsson | |
| 2008/0147202 A1 | 6/2008 | Danzig et al. | |
| 2008/0188949 A1 | 8/2008 | MacKenzie | |
| 2008/0221705 A1 | 9/2008 | Scussel | |
| 2008/0221706 A1 | 9/2008 | Scussel et al. | |
| 2008/0269914 A1 | 10/2008 | Coppens et al. | |
| 2009/0036999 A1 | 2/2009 | Egilsson et al. | |
| 2009/0069171 A1 | 3/2009 | Sagae | |
| 2009/0157196 A1 | 6/2009 | Danzig et al. | |
| 2009/0182435 A1 | 7/2009 | Haberman | |
| 2009/0198346 A1 | 8/2009 | Perkins et al. | |
| 2009/0240344 A1 | 9/2009 | Colvin et al. | |
| 2009/0306791 A1 | 12/2009 | Slemker et al. | |
| 2010/0070051 A1 | 3/2010 | Carstens | |
| 2010/0185300 A1 | 7/2010 | MacKenzie | |
| 2010/0249950 A1 | 9/2010 | Bielefeld | |

(56) References Cited

U.S. PATENT DOCUMENTS

| | | |
|---|---|---|
| 2010/0274364 A1 | 10/2010 | Pacanowsky et al. |
| 2010/0318196 A1 | 12/2010 | Egilsson |
| 2011/0029096 A1 | 2/2011 | Laghi |
| 2011/0035027 A1 | 2/2011 | McCarthy |
| 2011/0054635 A1 | 3/2011 | Watts |
| 2011/0071649 A1 | 3/2011 | McKinney |
| 2011/0077748 A1 | 3/2011 | Egilsson et al. |
| 2011/0118854 A1 | 5/2011 | Halldorsson |
| 2012/0041568 A1 | 2/2012 | MacKenzie |
| 2012/0095571 A1 | 4/2012 | Gunnarsson et al. |
| 2013/0053982 A1 | 2/2013 | Halldorsson |
| 2013/0138224 A1 | 5/2013 | MacKenzie |
| 2013/0197670 A1 | 8/2013 | MacKenzie |
| 2013/0331952 A1 | 12/2013 | Halldorsson et al. |
| 2015/0142133 A1 | 5/2015 | Egilsson et al. |
| 2017/0105853 A1 | 4/2017 | Jonsson et al. |
| 2017/0304085 A1 | 10/2017 | Kurth |

FOREIGN PATENT DOCUMENTS

| | | |
|---|---|---|
| DE | 745 981 C | 5/1944 |
| DE | 813 190 C | 9/1951 |
| DE | 1 795 809 U | 9/1959 |
| DE | 2 060 239 A1 | 6/1972 |
| DE | 2 127 269 A1 | 12/1972 |
| DE | 2 540 138 A1 | 3/1977 |
| DE | 2 544 446 A1 | 4/1977 |
| DE | 3 221 920 A1 | 4/1983 |
| DE | 3 508 919 A1 | 9/1986 |
| DE | 9 419 208 U1 | 1/1995 |
| EP | 0 631 765 A1 | 1/1995 |
| EP | 1 572 043 A2 | 9/2005 |
| EP | 2353550 A1 | 8/2011 |
| EP | 2745807 A1 | 6/2014 |
| EP | 2815728 A1 | 12/2014 |
| FR | 2 420 335 A1 | 10/1979 |
| FR | 2 539 616 A1 | 7/1984 |
| FR | 2 828 093 A1 | 2/2003 |
| GB | 263 377 A | 12/1926 |
| GB | 267 988 A | 3/1927 |
| GB | 826 041 A | 12/1959 |
| GB | 2 069 847 A | 9/1981 |
| GB | 2 087 727 A | 6/1982 |
| JP | H0623406 A | 2/1994 |
| JP | H07109314 A | 4/1995 |
| JP | H7-155343 A | 6/1995 |
| JP | H9-104714 A | 4/1997 |
| JP | 2637076 B2 | 8/1997 |
| JP | 97/34548 A2 | 9/1997 |
| JP | 2740503 B2 | 4/1998 |
| JP | H10-182740 A | 7/1998 |
| JP | 2001-055413 A | 2/2001 |
| JP | 2002-500697 A | 1/2002 |
| JP | 2006-176565 A | 7/2006 |
| JP | 2006-316160 A | 11/2006 |
| JP | 2006-528271 A | 12/2006 |
| JP | 3984304 B2 | 10/2007 |
| WO | 9734548 A2 | 9/1997 |
| WO | 00/74611 A2 | 12/2000 |
| WO | 01/54631 A1 | 8/2001 |
| WO | 01/67842 A1 | 9/2001 |
| WO | 02/26158 A2 | 4/2002 |
| WO | 03/024367 A2 | 3/2003 |
| WO | 03/024370 A1 | 3/2003 |
| WO | 03/039398 A2 | 5/2003 |
| WO | 03/099173 A1 | 12/2003 |
| WO | 2004/060136 A2 | 7/2004 |
| WO | 2010/085336 A1 | 7/2010 |
| WO | 2013/005735 A1 | 1/2013 |
| WO | 2015073793 A1 | 5/2015 |

OTHER PUBLICATIONS

Iceross Comfort Locking/Cushion Product Information Brochure, Mar. 27, 2009, 3 Pages.

Iceross Dermo, Product Information Sheets from Internet, http://www.ossur.com/prosthetics/liners/dermo, Mar. 27, 2009, 2 Sheets.

Military inStep: Prosthetic Socks and Liners, Product Information Sheets from Internet, http://www.amputee-coalition.org/military-instep/prosthetic-socks, Mar. 27, 2009, 3 Pages.

Prosthetic & Orthotic Update NewsLetter, No. 32, Internet Search Conducted Mar. 27, 2009, 4 Pages.

Walopur Platilon U, Product Information Brochure of Epurex Films GmbH & Co., KG, Internet Search Result Conducted Mar. 27, 2009, 2 Pages.

International Search Report and Written Opinion Issued in PCT/US2012/051645, dated Dec. 3, 2012.

Supplementary EP Search Report from EP Application No. 07837275.2, dated Feb. 19, 2014, 6 pages.

Extended European Search Report from EP Application No. 14161004.8, dated May 22, 2014, 6 pages.

Extended European Search Report from Corresponding Application No. 14163512.8, dated Jul. 30, 2014.

ESP Opti-Seal, Product Installation Instructions, http://www.wearesp.com, Downloaded Dec. 12, 2014, 1 page.

ESP Opti-Seal, "The Most Versatile Suspension System Availiable", www.wearesp.com, Downloaded Dec. 12, 2014, 2 pages.

ESP Secure-Ring System (SRS), http://www.wearesp.com, Downloaded Dec. 12, 2014, 1 page.

ESP Secure-Ring System (SRS), Product Instructions Sheet, http://www.wearesp.com, downloaded Dec. 12, 2014, 2 pages.

International Search Report from PCT Application No. PCT/US2016/055269, dated Jan. 4, 2017.

Eshraghi et al., "Gait Biomechanics of Individuals with Transtibial Amputation: Effect of Suspension System", PLoS One, vol. 9, Issue. 5, May 2014, 12 Pages.

Eshraghi et al., "Pistoning Assessment in Lower Limb Prosthetic Sockets", Prosthetics and Orthotics International, vol. 36, No. 1, 2012, pp. 15-24.

Gholizadeh et al., "Transtibial Prosthesis Suspension Systems: Systematic Review of Literature", Clinical Biomechanics vol. 29, 2014, pp. 87-97.

"Prosthetics Product Catalogue", Medi Prosthetics, www.medi-prosthetics.com, Jan. 2016, 184 pages.

"Verwendung and Verklebung Des LITE Vakuum-Ringes 5W700: Usage and Gluing of the 5W700 LITE Vacuum Ring", Wagner Polymertechnik GMBH, Sep. 6, 2016, 4 Pages.

International Search Report from PCT Application No. PCT/US2017/029063, dated Jul. 21, 2017.

"Slick SIL LSR," Surface Solutions Group LLC, retrieved from www.surfacesolutionsgroup.com on Mar. 30, 2017, 1 Page.

* cited by examiner

PROSTHETIC LINER

TECHNICAL FIELD

The disclosure relates to prosthetic liners adapted to provide an interface between a residual limb and a prosthetic socket.

BACKGROUND

The use of prosthetic liners adapted to provide an interface between a residual limb of an amputee and a hard socket to which a prosthetic device is secured is recognized in the art generally, as exemplified by U.S. Pat. No. 4,923,474.

Many conventional prosthetic liners are suspension liners adapted to secure the residual limb within the hard socket once the residual limb and liner are inserted into the socket in a close-fitting relationship. The distal region of these liners may include one or more seal elements arranged to engage the inner side of the socket and isolate the distal end area of the socket from atmosphere. Upon application of a pulling force on the liner relative to the socket, a suction is created in the distal end of the socket tending to retain the liner within the socket. Appropriate devices are usually provided to enable expulsion of air between the distal end of the liner and the hard socket, and to isolate the distal end of the hard socket from the atmosphere after the liner with a residual limb has been fully inserted within the hard socket.

According to a variation, the liner can be arranged as a locking liner provided with an umbrella at its distal end and a threaded socket for receiving a prosthetic securing pin member which then extends through an axial opening in the distal end of the hard socket.

While several prosthetic liner products exist, they have a number of drawbacks. For instance, anatomical variations in a residual limb tend to complicate and even compromise the seal formed between existing liners and the interior of the hard socket. In addition, radial movement or tilting of the residual limb within the socket is known to break or compromise the seal formed between the liner and the hard socket. With this loss of isolation, the connection between the residual limb and the hard socket can be unpredictable and/or inadequate, causing the user discomfort, grief and even injury.

There is thus a need for a prosthetic liner that provides a more reliable and comfortable connection between a residual limb and a prosthetic socket.

SUMMARY

The disclosure describes various embodiments of a prosthetic liner providing a construction and design that facilitates a more reliable and comfortable connection between a residual limb and a hard socket.

According to a variation, the prosthetic liner can include a flexible elongate, generally conical body portion formed from an elastomeric material. The body portion defines an inner surface and an outer surface forming a liner profile between a distal end and a proximal end. An axis extends between the distal and proximal ends. At least one seal element extends circumferentially about the axis and protrudes radially outward a distance from the liner profile. The at least one seal element has a seal height defined between the liner profile and a radially outward end of the at least one seal element.

The seal height varies circumferentially about the axis between a first seal height at a first circumferential position or a first circumferential region of the at least one seal element and a second seal height at a second circumferential position or a second circumferential region of the at least one seal element. This height variation of the at least one seal element advantageously allows the at least one seal element to compensate for radial movements of the residual limb within the socket. For instance, when inserted in a hard socket, the at least one seal element is compressed and bridges a seal between the body portion and an interior wall of the hard socket. In certain motion situations, such as when a user sits, the residual limb tends to tilt or reposition itself within the hard socket, which, in turn, can detach the at least one seal element from the interior wall of the socket. This potentially can break or compromise the seal formed between the liner and the hard socket. With this loss of isolation, the connection between the residual limb and the hard socket can be unpredictable and/or inadequate, causing the user discomfort, grief and even injury.

Where the at least one seal element is more likely to detach from the interior wall of the socket due to the repositioning of the residual limb, the at least one seal element can define a greater seal height so that even if the residual limb tilts or moves within the socket the at least one seal element can maintain its seal between the body portion and the interior wall. This advantageously makes the connection between the liner and socket more reliable and safer.

Further, the height variation of the at least one seal element can help the at least one seal element accommodate anatomical variations in the residual limb. For instance, in trans-tibial (TT) applications the tibia edge can be much less distinctive with strong, thicker residual limbs than with slender, skinnier residual limbs in which the tibia edge often defines the front of the residual limb quite dominantly. Consequently, the cross-sectional geometry of the residual limb deviates between a rounder shape and the more square or planar geometry of the tibia edge, which has a flattening medial to the tibia edge. Underlying the at least one seal element, this anatomical deviation or variation generally causes the residual limb to be spaced a greater radial distance from the interior of the socket in some portions of the tibia region than in the calf or other regions.

In an embodiment, the first seal height is greater than the second seal height and arranged to be positioned over the tibia region such that the at least one seal element can sufficiently bridge the seal across the greater radial distance between the user's tibia and the interior of the socket. Moreover, the increased seal height of the at least one seal element can be sized and selected to bridge the seal across an even greater radial distance if the residual limb tilts or moves within the socket. Thus, the varying seal height of the at least one seal element can bridge the seal across both larger and smaller radial distances between the residual limb and the interior of the socket, making the connection between the liner and the socket more reliable and comfortable.

According to a variation, the first seal height can be defined along the first circumferential region of the at least one seal element and subsequently decrease towards the second seal height defined along the second circumferential region of the at least one seal element opposite the first circumferential region. Thus, the greater first seal height extends along a greater length of the at least one seal element, increasing the size and strength of the seal between the first seal height of the at least one seal element and the socket. The first seal height can decrease continuously or incrementally toward the second seal height.

According to a variation, the body portion has a wall thickness that varies in the region of the at least one seal element around the circumference of the body portion. This varying wall thickness can be selected to protect or off-load pressure sensitive areas of a residual limb and/or to allow the body portion to better accommodate or correspond to the geometry of a residual limb.

BRIEF DESCRIPTION OF THE DRAWINGS

These and other features, aspects, and advantages of the present disclosure will become better understood regarding the following description, appended claims, and accompanying drawings.

DETAILED DESCRIPTION OF VARIOUS EMBODIMENTS

Figure 1:
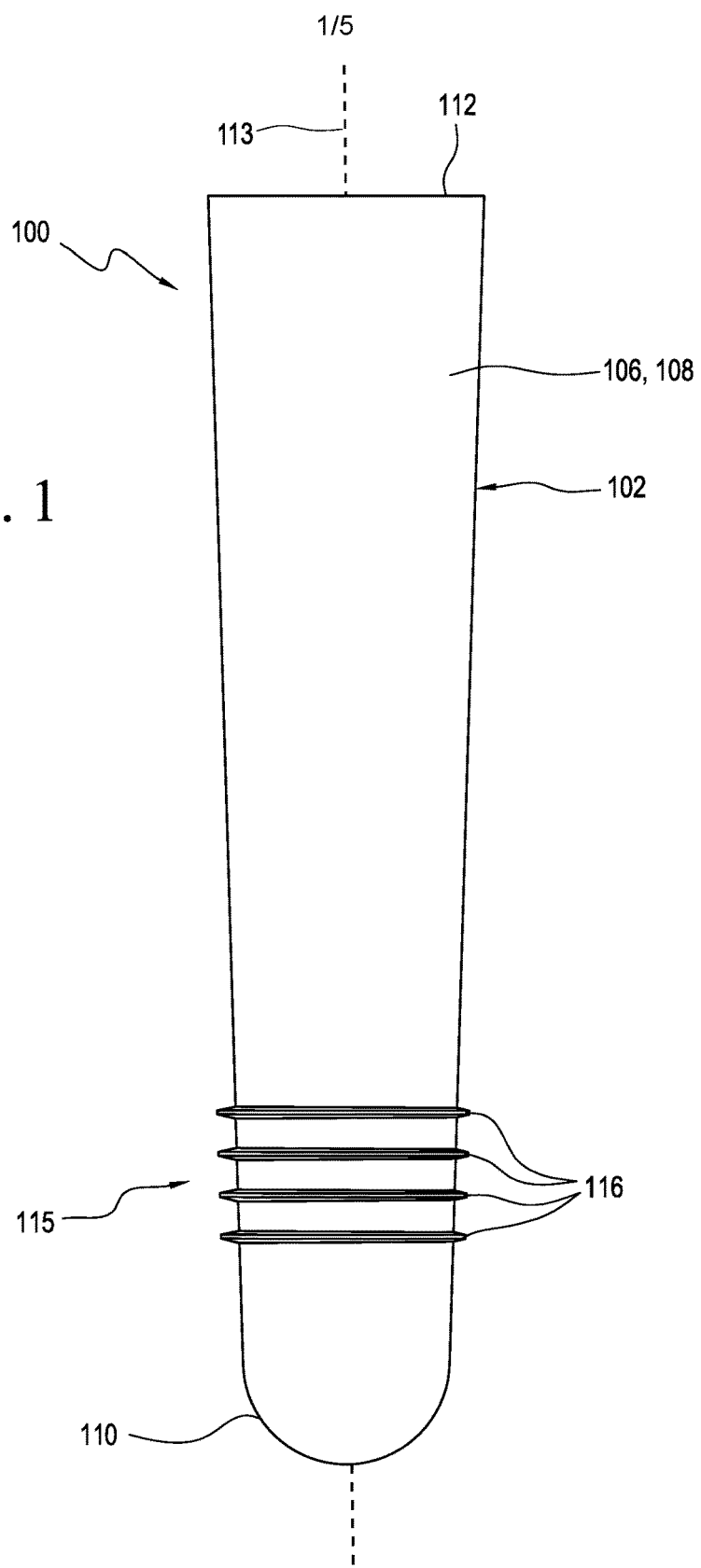
FIG. 1 is a side view of a prosthetic liner according to an embodiment.

A better understanding of different embodiments of the disclosure may be had from the following description read with the accompanying drawings in which like reference characters refer to like elements.

While the disclosure is susceptible to various modifications and alternative constructions, certain illustrative embodiments are in the drawings and are described below. It should be understood, however, there is no intention to limit the disclosure to the specific embodiments disclosed, but on the contrary, the intention covers all modifications, alternative constructions, combinations, and equivalents falling within the spirit and scope of the disclosure.

It will be understood that unless a term is expressly defined in this application to possess a described meaning, there is no intent to limit the meaning of such term, either expressly or indirectly, beyond its plain or ordinary meaning. Any element in a claim that does not explicitly state "means for" performing a specified function, or "step for" performing a specific function is not to be interpreted as a "means" or "step" clause as specified in 35 U.S.C. § 112(f).

Embodiments of the present disclosure provide a prosthetic liner having a construction and design that facilitates a more reliable and comfortable connection between a residual limb and a hard socket. It should be appreciated that the prosthetic liner of the present disclosure can be configured as a suspension liner, a locking liner, a cushion liner, combinations thereof, or any other suitable type of liner. Moreover, the liner is generally described as a trans-tibial (TT) prosthetic liner, however, in other embodiments, the liner can be arranged as a trans-femoral (TF) prosthetic liner, an upper limb prosthetic liner, or any other suitable liner.

FIG. 1 shows an embodiment of a prosthetic liner 100 comprising a suspension liner. The liner 100 includes a flexible elongate, generally conical body portion 102, formed from an elastomeric material such a silicone. The body portion 102 defines an inner surface 104 (shown in FIG. 2) and an outer surface 106 forming a liner profile 108 between a closed distal end 110 and an open proximal end 112. An axis 113 extends between the distal and proximal ends 110, 112.

Figure 2:
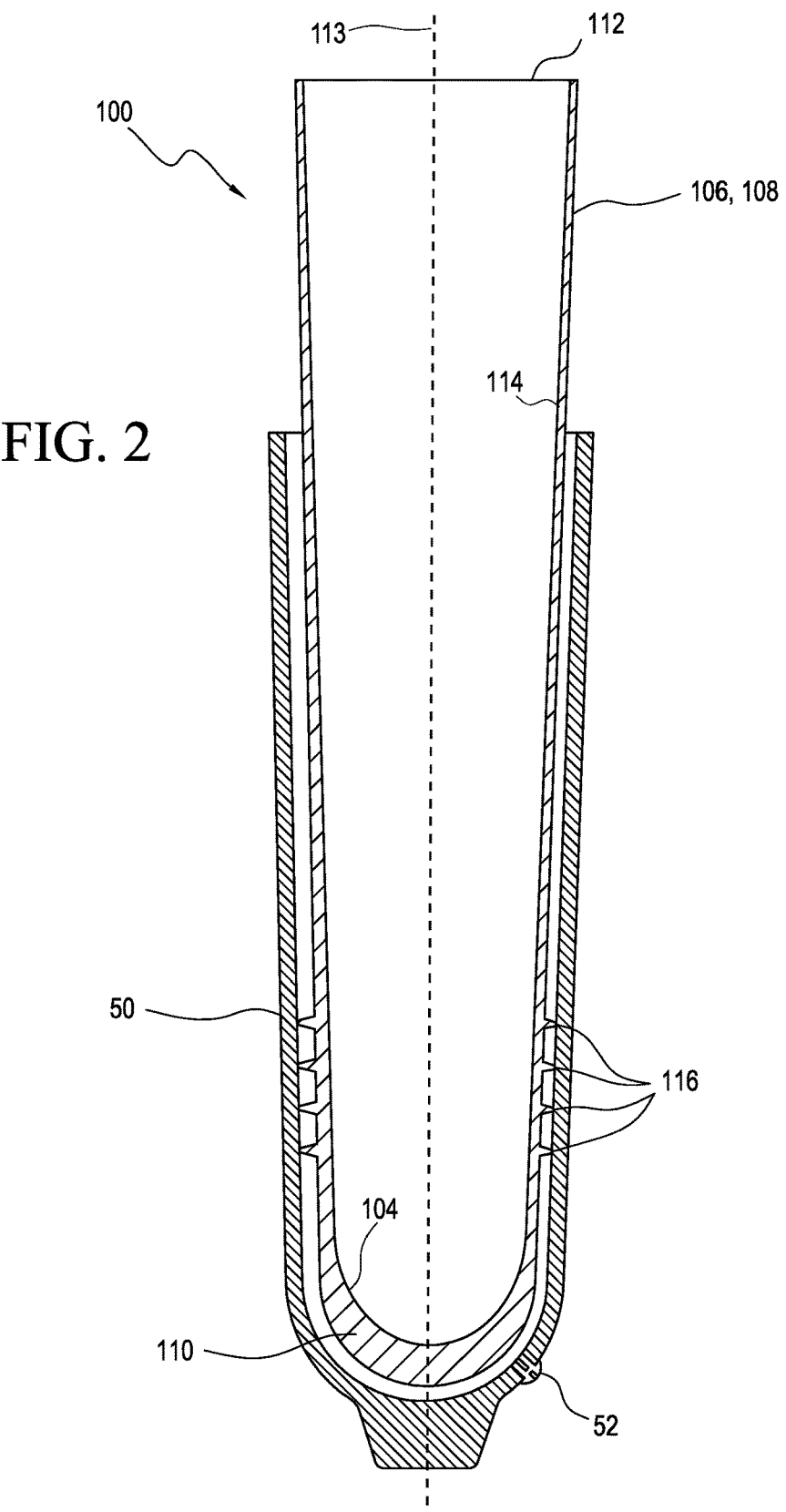
FIG. 2 is a cross section view of the liner in FIG. 1.

Referring to FIGS. 1 and 2, the body portion 102 can be soft and at least radially distensible elastically. The body portion 102 also may be elastically distensible axially or may have limited axial elasticity or at least greater elastic stiffness (resistance or distension) in an axial sense as compared with its radial elasticity, but such anisotropy is optional. If it is desired to increase the axial stiffness of the body portion 102, a reinforcement material 114 can be integrated into or attached to the elastomer of the body portion 102. For instance, the reinforcement material 114 can be attached to the inner surface 104 of the body portion 102. The reinforcement material 114 can comprise a textile reinforcement material embedded or bound to the silicone matrix of the body portion 102. The reinforcement material 114 can comprise a textile reinforcement material stretchable in an axial direction and a radial direction in a region proximal of the seal elements described below. Various reinforcement materials 114 may be utilized to limit axial distension of the body portion 102 and typically a material that is axially stiff but radially compliant is preferred.

The liner 100 is typically donned on a residual limb and the residual limb and the liner 100 are then inserted into a prosthetic socket 50 which is typically rigid or hard in order to carry loads transferred from a prosthetic device attached to the socket 50 to the residual limb and vice-versa.

The softer elastomer of the body portion 102 adheres to the skin of the residual limb frictionally to thereby secure the limb within the liner 100. The liner 100, on the other hand, remains contained within the hard socket 50 after it has been fully inserted to the distal end area of the hard socket effectively isolating the interior of the hard socket 50 from atmosphere. Any pulling forces applied to the liner 100 will result in a suction being created between the distal end of the liner 100 and the interior wall of the hard socket at its distal end area. Optionally, the socket 50 can include a valve assembly 52 arranged to enable expulsion of air between the distal end 110 of the liner 100 and the hard socket 50.

To further enhance isolation of the distal end area of the hard socket 50 from atmosphere, the body portion 102 includes a seal element region 115 having at least one seal element 116 extending circumferentially about the axis 113 and protruding radially outward from the liner profile 108.

Figure 3:
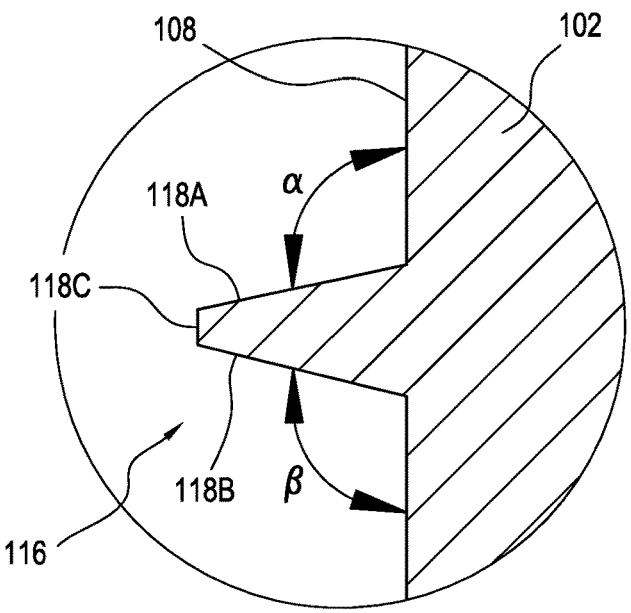
FIG. 3 is a detailed view of a seal element in FIG. 1 according to an embodiment.
Figure 4:
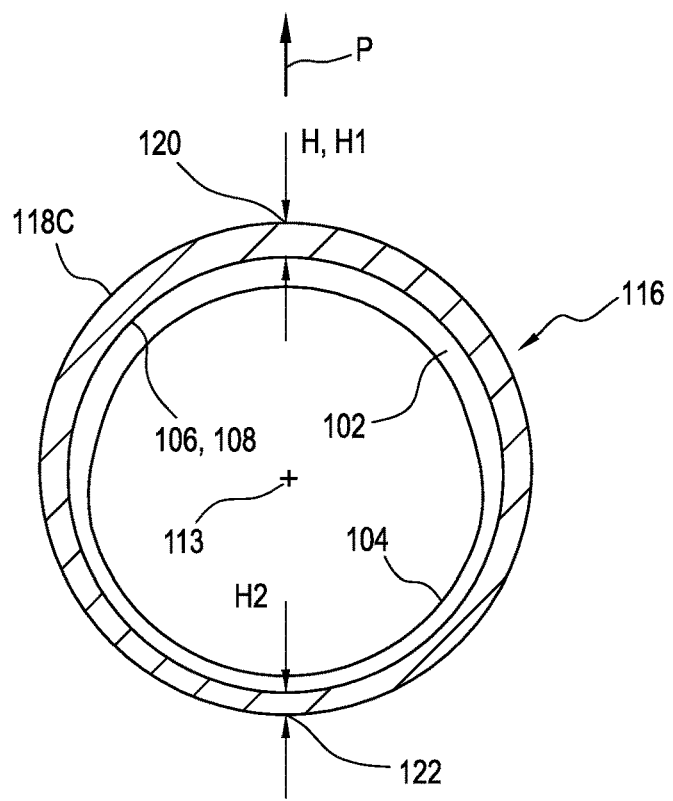
FIG. 4 is another cross section view of the liner in FIG. 1 through a seal element.

Referring to FIGS. 3 and 4, the at least one seal element 116 can have any suitable shape but is shown having a generally trapezoidal shape including two plane side areas 118A, 118B protruding radially outward from the liner profile 108 toward each other, and a radially outward end 118C. The radially outward end 118C is generally defined as the part or edge of the at least one seal element 116 that forms an outer radial boundary of the at least one seal element 116. In the illustrated embodiment, the radially outward end 118C comprises a plane outer end. In other embodiments, the radially outward end 118C can comprise a peak, a crest, a rounded surface, or other suitable part of the seal element 116.

An angle α is defined between the liner profile 108 and the side area 118A and an angle β is defined between the liner profile 108 and the side area 118B. The angle α and the angle β can be the same. The angle α and the angle β can be different. The angle α and the angle β can be oblique.

The at least one seal element 116 can be formed of the same elastomeric or silicone material as the body portion 102 and/or can be created integrally in one piece with the body portion 102 during molding or forming of the body portion 102. In other embodiments, the at least one seal element 116 can be formed separately of a softer or stiffer material or a material more suitable for a seal than the material forming the body portion 102, and then secured to the liner 100.

The at least one seal element 116 can be formed in any suitable manner. For instance, the at least one seal element 116 can be formed via a casting mold using a profile cutter or an electro-erosion electrode. The angle at which a base of the at least one seal element 116 meets the body portion 102 can be independent of an insertion depth of a forming tool which introduces the seal element groove into the casting mold Other examples of the at least one seal element 116 can be found in U.S. Pat. Nos. 9,060,885, 9,066,821, and 8,911,506, each incorporated by reference and belonging to the assignee of this disclosure.

As noted above, the at least one seal element 116 extends circumferentially about the axis 113 and protrudes radially outward from the liner profile 108. When inserted in the hard socket 50 (shown in FIG. 2), the at least one seal element 116 is compressed and bridges a seal between the body portion 102 and an interior wall of the hard socket 50, helping to generate a suction between the distal end of the liner 100 and the interior wall of the socket 50.

The at least one seal element 116 includes a seal height H defined between the liner profile 108 and the radially outward end 118C of the at least one seal element 116. More particularly, the seal height H is the distance between the liner profile 108 and the radially outward end 118C measured normal to the liner profile 108. As described in more detail below, the seal height H varies circumferentially about the axis 116 to help maintain the seal between the body portion 102 and the hard socket 50 in different motion situations.

FIG. 4 is a cross-section view of the liner 100 through the at least one seal element 116. The arrow P indicates the front side of the liner 100, i.e. the frontal direction. The liner 100 is arranged to be worn such that the front side of the liner 100 is located on the front side of the residual limb. In the case of a trans-tibial amputee, the liner 100 is arranged to be worn such that the front side of the liner 100 is located on the front of the tibia edge or shin bone edge.

As shown, the seal height H varies between a first seal height H1 located at a first circumferential position 120 on the at least one seal element 116 and a second seal height H2 located at a second circumferential position 122 on the at least one seal element 116. The first and second circumferential positions 120, 122 are generally defined as points on the at least one seal element 116 circumferentially distributed around the axis 113.

As shown, the first circumferential position 120 corresponds to a frontal circumferential position on the body portion 102 and the second circumferential position 122 corresponds to a rear circumferential position on the body portion 102. The first circumferential position 120 can be offset about 180 degrees from the second circumferential position 122.

The height H can vary continuously or incrementally between the first and second seal heights H1, H2. The first seal height H1 can be greater than the second seal height H2.

The first seal height H1 can be a maximum height value and the second seal height H2 can be a minimum height value. In an embodiment, the first seal height H1 can be between about 3 mm and about 9 mm, about 4 mm and about 8 mm (e.g., about 6 mm). It will be appreciated that in other embodiments the first seal height H1 can be more or less. In an embodiment, the second seal height H2 can be between about 1 mm and about 6 mm or about 2 mm and about 5 mm (e.g., about 4 mm). It will be appreciated in other embodiments the second seal height H2 can be more or less.

In an embodiment, the first seal height H1 can decrease starting from the first circumferential position 120 on the at least one seal element 116 to the second seal height H2 at the second circumferential position 122. On both sides of the first circumferential position 120, the seal height H of the at least one seal element 116 continuously decreases from the first seal height H1 toward the second seal height H2.

The height variation of the at least one seal element 116 beneficially helps the at least one seal element 116 to compensate for radial movements of the residual limb within the socket 50. For instance, when inserted in the socket 50, the at least one seal element 116 is compressed and bridges a seal between the body portion 102 and an interior wall of the hard socket 50. In certain motion situations, such as when a user sits, the residual limb tends to tilt or reposition itself within the hard socket 50, which, in turn, could potentially detach the seal element from the interior wall of the socket 50. This could break or compromise the seal formed between the liner and the hard socket. With this loss of isolation, the connection between the residual limb and the hard socket can be unpredictable and/or inadequate, causing the user discomfort, grief and even injury.

Where the at least one seal element 116 is more likely to detach from the interior wall of the socket 50, the greater first seal height H1 can be positioned and sized so that even if the residual limb tilts or moves within the socket the at least one seal element 116 maintains its seal between the body portion 102 and the interior wall of the socket 50. This advantageously makes the connection between the liner 100 and the socket 50 more reliable and safer.

Further, the seal height H can vary to help the at least one seal element 116 accommodate anatomical variations of the residual limb. For instance, in trans-tibial applications, the tibia edge can be much less distinctive with strong, thicker residual limbs than with slender, skinnier residual limbs in which the tibia edge often defines the front of the residual limb quite dominantly. Consequently, the cross-sectional geometry of the residual limb deviates between a rounder geometry and a more square or planar geometry of the tibia edge, which has a flattening medial to the tibia edge. Underlying the at least one seal element 116, this anatomical deviation or variation generally causes the residual limb to be spaced a greater radial distance from the interior of the socket in some portions of the tibia region (e.g., the flattening medial to the tibia edge) than in the calf or other regions.

In an embodiment, the greater first seal height H1 of the at least one seal element 116 is arranged to be worn over the tibia region so that the at one least seal element 116 sufficiently bridges the seal across the greater radial distance between the user's tibia and the interior of the socket 50. Moreover, the greater first seal height H1 is sized and selected to maintain the seal across an even greater radial distance between the user's tibia and the interior of the socket 50 if the residual limb tilts or moves within the socket 50.

Further, the lesser second seal height H2 of the at least one seal element can allow the at least one seal element 116 to both maintain the seal against the interior wall of the hard socket 50 and more comfortably accommodate movement of the rear of the residual limb toward the interior wall of the hard socket 50. For instance, the second seal height H2 can be selected to reduce the likelihood of pressure points on the residual limb. If the second seal height H2 of the at least one seal element 116 is too great, the at least one seal element 116 can undesirably bunch or fold over onto itself when compressed between the rear of the residual limb and the interior wall of the socket 50, creating uncomfortable and potentially dangerous pressure points on the residual limb.

Thus, the varying seal height H of the at least one seal element 116 is adapted to bridge the seal across both varying radial distances between the residual limb and the interior of the socket 50, making the connection between the liner 100 and the socket 50 more reliable and comfortable.

By controlling the relationship between the first seal height H1 and the second seal height H2 of the at least one seal element 116, the liner 100 can thus beneficially create both a more reliable and comfortable connection between the liner 100 and the socket 50. In an embodiment, the first seal height H1 can between about 1.1 and about 2, about 1.3 and about 1.8, or about 1.4 and about 1.6 times greater than the second seal height H2. In other embodiments, the first seal H1 can be more or less relative to the second height H2.

According to a variation, the first seal height H1 and/or the second seal height H2 can be selected or customized based on user specific measurements of radial displacement between the body portion 102 or residual limb and the interior wall of the socket 50 in the region of the at least one seal element 116. In other embodiments, the first seal height H1 and/or the second seal height H2 can be selected based on common radial displacement values between the body portion 102 or residual limb and the interior wall of the socket 50 in the region of the at least one seal element 116.

In an embodiment, the height variation of the seal element 116 can help account for volume and/or shape fluctuations of a residual limb during use. For instance, if the volume of a residual limb decreases during a period of use, the greater first seal height H1 of the seal element 116 can help compensate for the volume decrease of the residual limb within the socket 50. This reduces the likelihood of losing the seal between the body portion 102 and the hard socket 50, making the connection between the liner 100 and the socket 50 more reliable during use.

It will be appreciated that the varying seal height H of the seal element 116 described is exemplary only, as any suitable number and/or arrangement of seal height variations are possible. For instance, the lesser seal height H2 can be arranged for positioning over anatomical variations of a residual limb such as bony protuberances. In other embodiments, the greater seal height H1 can be arranged for positioning over sensitive areas on a residual limb or depressions defined in a residual limb. In yet other embodiments, the greater seal height H1 can be located on the lateral and/or medial sides of the seal element 116.

Referring again to FIGS. 1 and 2, the at least one seal element 116 can comprise a plurality of seal elements 116 axially spaced along the body portion 102. This advantageously may distribute traction more evenly than a single seal system. It also beneficially may reduce the likelihood of creating localized pressure peaks on the residual limb. It will be appreciated that the height H of only one, several, or all of the sealing elements 116 may vary. In an embodiment, the seal elements 116 can include 4 seal elements. In other embodiments, the seal element 116 can include two, three, or any other suitable number of seal elements. The at least one seal element 116 is preferably located toward the distal end 110 but can be located anywhere along the axis 113.

Figure 5:
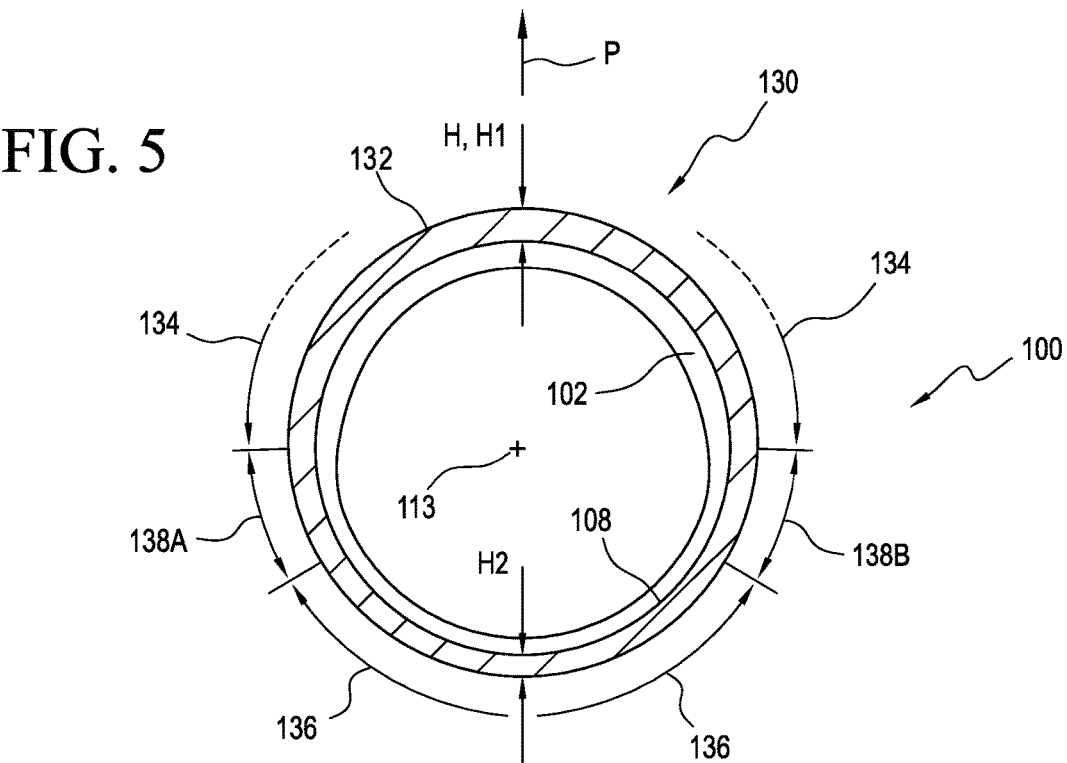
FIG. 5 is a cross section view of a prosthetic liner through a seal element according to another embodiment.
Figure 6:
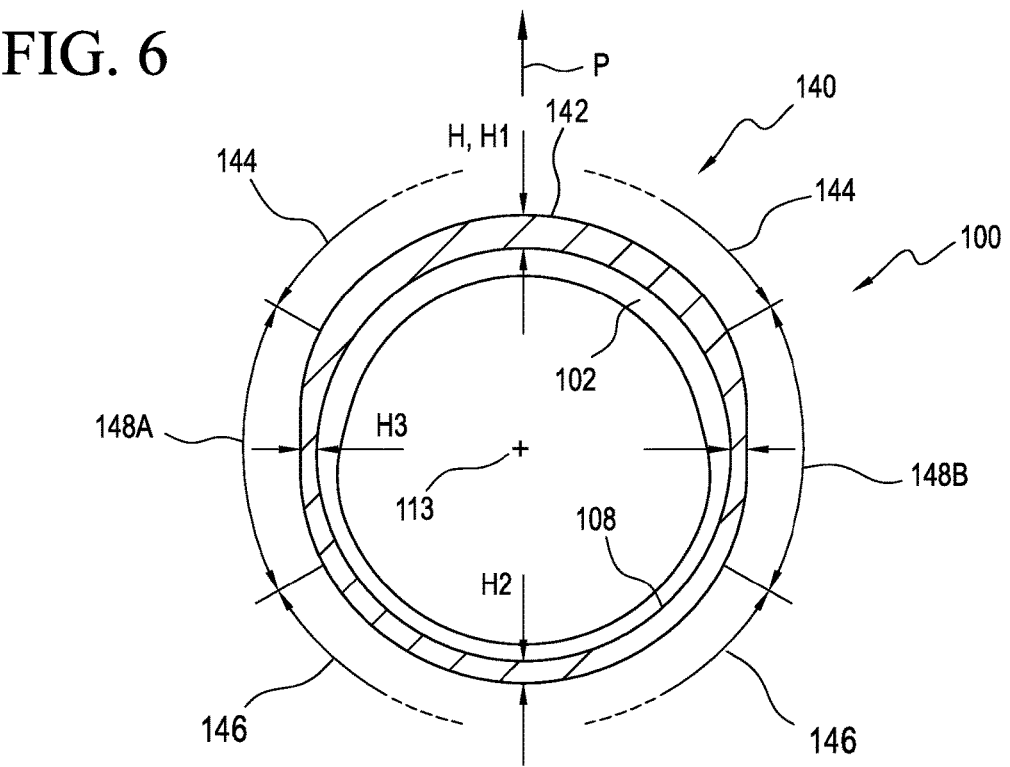
FIG. 6 is a cross section view of a prosthetic liner through a seal element according to another embodiment.

With reference to FIGS. 5 and 6, alternative embodiments of the at least one seal element shown in FIGS. 1-4 are shown. FIG. 5 shows a seal element 130 according to another embodiment that extends circumferentially about the axis 113 and protrudes radially outward from the liner profile 108. When inserted into a hard socket, the at least one seal element 130 is compressed and bridges a seal between the body portion 102 and the hard socket.

The seal element 130 includes a seal height H defined between the liner profile 108 and a radially outward end 132 or outer radial boundary of the seal element 130. More particularly, the seal height H is the distance between the liner profile 108 and the radially outward end 132 measured normal to the liner profile 108. Similar to other embodiments, the seal height H varies along the circumference of the seal element 130. As shown, the seal height H can vary between a first seal height H1 defined along a first circumferential region 134 of the seal element 130 and a second seal height H2 defined along a second circumferential region 136 of the seal element 130. The first and second circumferential regions 134, 136 are generally defined as portions of the seal element 130 circumferentially extending a distance around the axis 113. First and second transition regions 138A, 138B extend between the first circumferential region 134 and the second circumferential region 136.

In an embodiment, the first circumferential region 134 of the seal element 130 is located along a frontal region of the body portion 102 and the second circumferential region 136 of the seal element 130 is located along a rear region of the body portion 102 opposite the frontal region of the body portion 102. The first circumferential region 134 can be angularly offset from the second circumferential region 136. For instance, the first circumferential region 134 can be angularly offset from the second circumferential region 136 about 180 degrees. The first circumferential region 134 can be opposite the second circumferential region 136.

The first circumferential region 134 can have a same or different length than the second circumferential region 136. For instance, the length of the second circumferential region 136 can be less than the length of the first circumferential region 134 or vice versa. Similarly, the length of the first and second transition regions 138A, 138B can be the same or different and will vary based on the lengths of the first and second circumferential regions 134, 136. For instance, if the lengths of the first and second circumferential regions 134, 136 are greater, the lengths of the transition regions 138A, 138B will be shorter. The position of the first and second transition regions 138A, 138B will also vary based on the lengths and/or positions of the first and second circumferential regions 134, 136.

In an embodiment, the first seal height H1 can be generally constant along the first circumferential region 134 and the second seal height H2 can be generally constant along the second circumferential region 136. In other embodiments, the first seal height H1 and/or the second seal height H2 can vary along the first and second circumferential regions 134, 136.

The first seal height H1 can be greater than the second seal height H2. The height H can decrease starting from the first seal height H1 along the first circumferential region 134 of the seal element 130 to the second seal height H2 along the second circumferential region 136 of the seal element 130. According to a variation, the first seal height H1 can be a maximum height value and the second seal height H2 can be a minimum height value. The first and second seal heights H1, H2 can be sized and selected as described above.

The seal height H can vary or decrease from the first seal height H1 in at least one of the transition regions 138A, 138B. The first seal height H1 in the first circumferential region 134 can decrease to the second seal height H2 in the second circumferential region 136.

In an embodiment, the seal height H along one or more portions of at least one of the transition regions 138A, 138B can be less than the second seal height H2 in the second circumferential region 136 of the seal element 130. In other embodiments, the seal height H along one or more portions of at least one of the transition regions 138A, 138B can be greater than the first seal height H1 in the first circumferential region 134. The seal height H of the seal element 130 along the first and second transition regions 138A, 138B can constantly decrease from the first seal height H1 toward the second seal height H2. In other embodiments, the seal height H of the seal element 130 along the first and second transition regions 138, 140 can decrease incrementally from the first seal height H1 toward the second seal height H2.

Similar to the seal element 116, the seal height differential of the seal element 130 can advantageously create both a more reliable and more comfortable connection between the residual limb and the socket. Further, because the first seal height H1 of the first circumferential region 134 extends a distance around the axis 113, the size and strength of the seal between the first seal height H1 of the seal element 130 and the front of the socket 50 is enhanced. Moreover, the first seal height H1 of the first circumferential region 134 may accommodate multiple anatomical variations and/or compensate for movement of the residual limb within the socket 50 over a greater area between the body portion 102 and the socket 50.

Likewise, because the second seal height H2 of the second circumferential region 136 extends a distance around the axis 113, the size and strength of the seal between the second seal height H2 of the seal element 130 and the back of the socket is enhanced.

FIG. 6 shows a seal element 140 according to yet another embodiment. The seal element 140 can be similar to the seal element 130. The seal element 140 includes a seal height H defined between the liner profile 108 and a radially outward end 142 of the seal element 140. The seal height H includes a first seal height H1 defined along a first circumferential region 144 of the seal element 140 and a second seal height H2 defined along a second circumferential region 146 of the seal element 140. The first circumferential region 144 is located on a frontal region of the body portion 102 and the second circumferential region 146 is located on a rear region of the body portion 102. The first seal height H1 is constant or substantially constant along the first circumferential region 144 and the second seal height H2 is constant or substantially constant along the second circumferential region 146.

Similar to the seal element 130, the seal element 140 includes first and second transition regions 148A, 148B extending between the first circumferential region 144 and the second circumferential region 146. At least one of the first or second transition regions 148A, 148B defines a third seal height H3 along the lateral and/or medial side of the body portion 102. The third seal height H3 can vary along the first or second transition regions 148A, 148B.

The third seal height H3 of the first and/or second transition regions 148A, 148B can be less than the second seal height H2 of the second circumferential region 146. The third seal height H3 of the first and/or second transition regions 148A, 148B can be greater than the first seal height H1 of the first circumferential region 144.

According to a variation, the third seal height H3 is less than both the first seal height H1 of the first circumferential region 144 and the second seal height H2 of the second circumferential region 146. This lateral/medial height reduction of the seal element 140 can reduce the overall profile of the seal element 140 without compromising the sealing effect of the seal element 140. This is advantageous because tilting or radial movement of the residual limb in the socket from side to side usually occurs to a lesser degree and thus a lower seal height is appropriate in the lateral/medial regions. The lateral/medial height reduction of the seal element 140 can also be selected to accommodate anatomical variations of the residual limb.

Embodiments of the present disclosure may also include one or more other features adapted to help provide a more reliable and comfortable connection between a residual limb and a prosthetic socket. For instance, a thickness of the body portion between the liner profile and the inner surface in the seal elements region 115 may be varied to better accommodate the fit of the residual limb within the socket. Generally, a liner body portion is arranged to be thin-walled because a wall thickness that is too great can wrinkle upon bending of the knee, creating discomfort for the user. On the other hand, if the wall thickness is too thin, a pressure load can be applied to the residual limb in the region of the seal elements, aggravating the residual limb and/or resulting on lesions.

Figure 7:
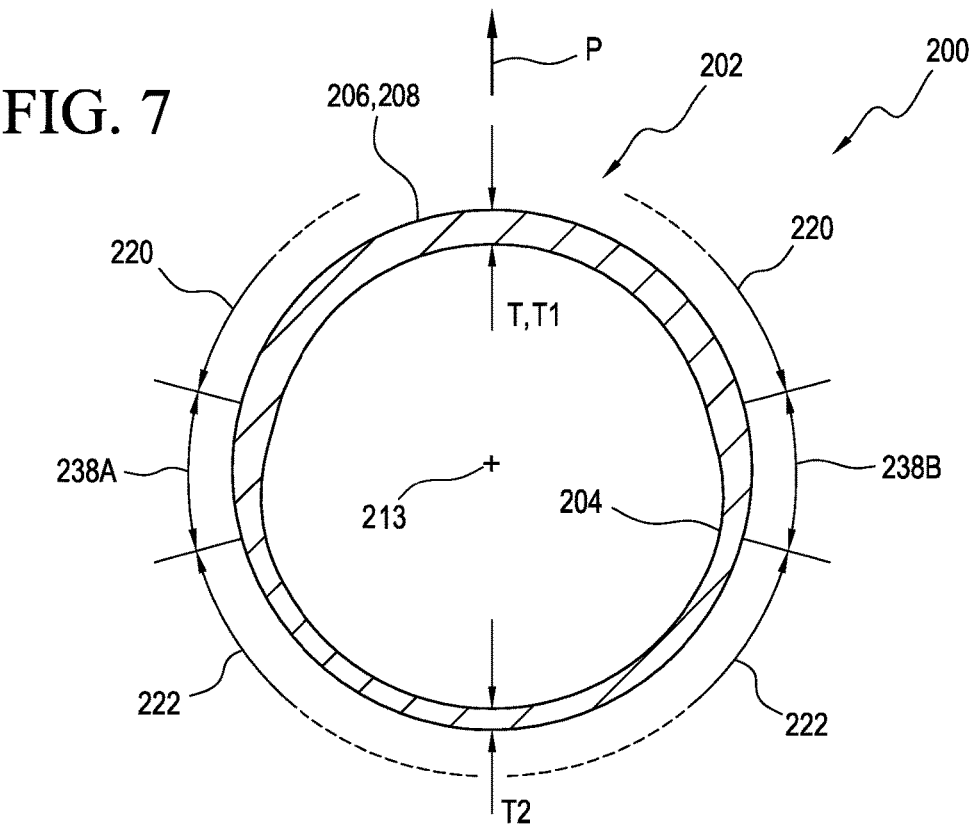
FIG. 7 is a cross section view of a prosthetic liner through a seal element according to another embodiment.

FIG. 7 is a cross section of a prosthetic liner 200 according to another embodiment. The liner 200 can be similar to the liner 100, including a body portion 202 defining an inner surface 204 and an outer surface 206 forming a liner profile 208. Similar to the other embodiments, the body portion 202 can include at least one seal element configured similar to any of the seal elements described herein.

The body portion 202 includes a wall thickness T defined between the inner surface 204 and the liner profile 208. The arrow P indicates the front side of the liner 200. The liner is arranged to be worn such that the front side of the liner 200 is located on the front side of the residual limb.

As shown, the wall thickness T of the body portion 202 can vary circumferentially about an axis 213. For instance, the wall thickness T can vary from a first thickness T1 along a first body circumferential region 220 of the body portion 202 to a second thickness T2 along a second body circumferential region 222 of the body portion 202. The first and second body circumferential regions 220, 222 are portions of the body portion 202 circumferentially extending a distance around the axis 213.

The wall thickness T can be greater in the region of a first seal height (e.g., the first seal height H1) of the at least one seal element than in the region of a second seal height (e.g., the second seal height H2) of the at least one seal element.

The first thickness T1 can be constant or substantially constant along the first body circumferential region 220 and the second thickness T2 can be constant or substantially constant along the second body circumferential region 222. The wall thickness T varies or transitions between first and second thicknesses T1, T2 through first and second transition regions 238A, 238B extending between the first body circumferential region 220 and the second body circumferential region 222. The first and second transition regions 238A, 238B can be located along the lateral and medial sides of the body portion 202.

The first body circumferential region 220 is located in a frontal region of the body portion 202 and the second body circumferential region 222 is located generally opposite the frontal region. According to a variation, the first body circumferential region 220 can be radially stiffer than other portions of the body portion 202. This greater radial stiffness can be achieved at least by increasing the thickness T of the body portion 202 through the first body circumferential region 220. Conversely, greater radial flexibility of the body portion 202 can be achieved at least by decreasing the thickness T at certain portions of the body portion 202. For instance, the first thickness T1 along the first body circumferential region 220 can be greater than the second thickness T2 along the second body circumferential region 222.

Because the wall thickness T in the frontal region of the body portion 202 is thicker and therefore stronger relative to other regions of the body portion 202, the liner 200 can better protect a user's pressure sensitive areas (e.g., the shin bone) underlying this thickened region, increasing user comfort. This increased wall thickness T also allows the body portion 202 to better accommodate or correspond to the geometry of a residual limb which typically deviates from a round shape.

According to a variation, the wall thickness T only varies in the region of the seal elements. For instance, the wall thickness T can decrease in a proximal direction from a seal element region (e.g., seal element region 115 shown in FIG. 1) of the liner 200. In other embodiments, above or proximal to the seal element region, the body portion 202 can have a circumferentially uniformly thin wall thickness (e.g., the second thickness T2) so that, for example, over the knee there is not excessive or too much body portion material. This beneficially can reduce the likelihood of the body portion 202 aggravating a user's knee during bending such as along the rear of the back of the knee.

In an embodiment, below or distal to the seal element region, the wall thickness variation of the seal element region can be maintained or a circumferentially uniformly thin wall thickness can be provided.

The length of the first body circumferential region 220 can be the same or different than the second body circumferential region 222. The first body circumferential region 220 can correspond to a first circumferential region of the seal element (e.g., the first circumferential region 144) and the second body circumferential region 222 can correspond to a second circumferential region of the seal element (e.g., the second circumferential region 146).

Figure 8:
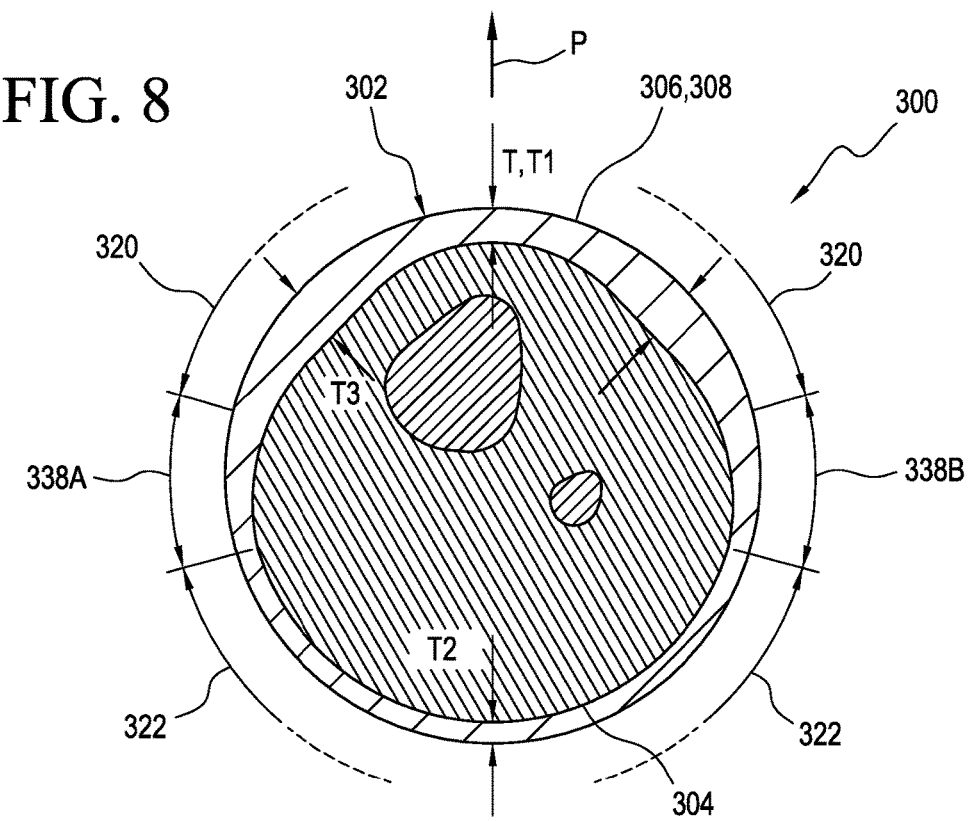
FIG. 8 is a cross section view of a prosthetic liner through a seal element according to another embodiment.

FIG. 8 is a cross section of a prosthetic liner 300 according to yet another embodiment. The liner 300 can include a body portion 302 defining an inner surface 304 and an outer surface 306 forming a liner profile 308. Similar to the other embodiments, the body portion 302 can include at least one seal element configured similar to any of the seal elements described herein.

The body portion 302 includes a wall thickness T defined between the inner surface 304 and the liner profile 308. The arrow P indicates the front side of the liner 300. The liner 300 is arranged to be worn such that the front side of the liner 300 is located on the front side of the residual limb.

As shown, the wall thickness T of the body portion 302 can include a first thickness T1 along a first body circumferential region 320 and a second thickness T2 along a second body circumferential region 322. The first thickness T1 is greater than the second thickness T2.

The wall thickness T in a region between the first and second body circumferential regions 320, 322 can vary. For instance, the wall thickness T in a region between the first and second body circumferential regions 320, 322 can increase from the first body circumferential region 320 or the second body circumferential region 322. In other embodiments, the wall thickness T in a region between the first and second body circumferential regions 320, 322 can decrease from the first body circumferential region 320 or the second body circumferential region 322.

As shown, the first body circumferential region 320 can define a third thickness T3 extending circumferentially toward ends of the first body circumferential region 320. According to a variation, the third thickness T3 is greater than the first thickness T1. For instance, the third thickness T3 can be between about 1.1 and about 2, about 1.2 and about 1.8, or about 1.4 and about 1.6 times the T1. In other embodiments, the third thickness T3 can be greater than about 0.6 mm, about 0.7 mm, 0.8 mm, or about 0.9 mm.

From the circumferential ends of the first body circumferential region 320, the wall thickness T can decrease from the third thickness T3 toward the second thickness T2 along a rear region of the liner 300. This decrease in the wall thickness T can occur through first and second transition regions 338A, 338B as shown.

In the illustrated embodiment, the third thickness T3 causes the wall thickness T of the body portion 302 medial and lateral of a user's tibia edge to be thickened radially inwardly. This beneficially allows the body portion 302 to better accommodate anatomical variations of the residual limb. For instance, as the liner 300 is forced against the front region of the residual limb within a hard socket, the wall including the third thickness T3 can engage the residual limb along the medial and lateral sides of the tibia edge and support the wall including the first thickness T1 over the tibia edge, which, in turn, allows the liner 300 to exert or transfer a greater force on the residual limb along the medial and lateral sides of the tibia edge rather than directly on the tibia edge. This advantageously at least in part off-loads pressures on the tibia edge, thereby enhancing comfort of the liner 300.

The first thickness T1, the second thickness T2, and/or the third thickness T3 can be constant or can vary. For instance, the third thickness T3 can increase toward a circumferential middle section. In other embodiments, the third thickness T3 can both increase and decrease. In other embodiments, the third thickness T3 can be sized and positioned based on anatomical variations defined by a specific residual limb (e.g., bony protuberances).

Moreover, the third thickness T3 is described extending along both the lateral and medial sides of the body portion 302 but it will be appreciated that the third thickness T3 can extend circumferentially along any suitable region of the body portion 302. For instance, the third thickness T3 can extend along the medial side and not the lateral side or vice versa. In other embodiments, the third thickness T3 can be located along the front region of the liner 100 or the rear region of the liner 100.

While the liners of the present disclosure are generally described including at least one seal element, in other embodiments, the at least one seal element may be omitted. For instance, the liner can be configured as a locking liner or a cushion liner without seal elements and including a body portion having a varying wall thickness arranged to better accommodate anatomical variations of the residual limb.

Further, while various aspects and embodiments have been disclosed herein, other aspects and embodiments are contemplated. The various aspects and embodiments disclosed herein are for purposes of illustration and are not intended to be limiting. Additionally, the words "including," "having," and variants thereof (e.g., "includes" and "has") as used herein, including the claims, shall be open ended and have the same meaning as the word "comprising" and variants thereof (e.g., "comprise" and "comprises").

The invention claimed is:

1. A prosthetic liner adapted to provide an interface between a residual limb and a prosthetic socket, the prosthetic liner comprising:
   a flexible elongate, generally conical liner body portion formed from an elastomeric material, the body portion defining an inner surface, an outer surface forming a liner profile between a closed distal end and an open proximal end, and an axis extending between the distal end and proximal end; and
   at least one seal element extending circumferentially about the axis and protruding radially outward a distance from the liner profile, the at least one seal element having a seal height defined between the liner profile and a radially outward end of the at least one seal element, the seal height varying circumferentially around the axis between a first seal height at a first circumferential position or a first circumferential region of the at least one seal element and a second seal height at a second circumferential position or a second circumferential region of the at least one seal element.

2. The prosthetic liner of claim 1, wherein the first seal height is greater than the second seal height and the first circumferential position of the at least one seal element is located along a front region of the body portion.

3. The prosthetic liner of claim 1, wherein the first seal height is greater than the second seal height and the first circumferential position is located along a lateral region or a medial region of the body portion.

4. The prosthetic liner of claim 1, wherein the first seal height is between about 1.3 and about 1.8 times greater than the second seal height.

5. The prosthetic liner of claim 2, wherein the first seal height is substantially constant along the first circumferential region and the second seal height is substantially constant along the second circumferential region.

6. The prosthetic liner of claim 1, wherein the seal height includes a third seal height greater than the first and second seal heights.

7. The prosthetic liner of claim 6, wherein the third seal height extends along only one side of the body portion.

8. The prosthetic liner of claim 6, wherein the third seal height extends along both the lateral and medial sides of the body portion.

9. The prosthetic liner of claim 1, wherein the body portion includes a wall thickness defined between the inner surface of the body portion and the liner profile and varies in a region of the at least one seal element.

10. The prosthetic liner of claim 9, wherein the wall thickness includes a first thickness along a first body circumferential region and a second thickness along a second body circumferential region, the first thickness being greater than the second thickness.

11. The prosthetic liner of claim 10, wherein the first body circumferential region comprises a front region of the body portion and the second body circumferential region comprises a rear region of the body portion opposite the front region.

12. The prosthetic liner of claim 11, wherein the first thickness is between about 1.2 and about 1.8 times greater than the second thickness.

13. The prosthetic liner of claim 10, wherein the first thickness transitions to the second thickness along lateral and medial sides of the body portion.

14. The prosthetic liner of claim 9, wherein the wall thickness includes a third thickness different than the first thickness and the second thickness.

15. The prosthetic liner of claim 1, wherein the at least one seal element comprises a plurality of seal elements and the seal height of at least one of the seal elements is constant.

16. A prosthesis system comprising:
   a prosthetic socket adapted to a shape of a residual limb; and
   a prosthetic liner adapted to provide an interface between the residual limb and the prosthetic socket, the liner including:
      a flexible elongate, generally conical body portion formed from an elastomeric material, the body portion defining an inner surface, an outer surface forming a liner profile between a distal end area and a proximal end area, and an axis extending between the distal end area and the proximal end area; and
      at least one seal element extending circumferentially about the axis and protruding radially outward from the liner profile, the at least one seal element arranged to bridge a seal between the prosthetic socket and the body portion, and having a seal height defined between the liner profile and a radially outward end of the at least one seal element, the seal height varying circumferentially around the axis between a first seal height and a second seal height.

17. The prosthesis system of claim 16, wherein the first seal height of the at least one seal element is located along a front region of the body portion, and the second seal height of the at least one seal element is located along a rear region of the body portion opposite the front region.

18. The prosthesis system of claim 17, wherein the first seal height is between about 1.3 and about 1.8 times greater than the second seal height.

19. A method of positively securing a residual limb within a prosthetic socket, the method comprising:
   donning a prosthetic liner on a distal end of the residual limb, the prosthetic liner including:
      a flexible elongate, generally conical body portion formed from an elastomeric material, the body portion defining an inner surface, an outer surface forming a liner profile between a distal end area and a proximal end area, and an axis extending between the distal end area and the proximal end area; and
      at least one seal element extending circumferentially about the axis and protruding radially outward a distance from the liner profile, the at least one seal element having a seal height defined between the liner profile and a radially outward end of the at least one seal element; and
   inserting the prosthetic liner and the distal end of the residual limb into a prosthetic socket such that the at least one seal element engages an interior wall of the prosthetic socket and deforms to bridge a substantially air-tight seal between the prosthetic socket and the body portion, wherein the seal height of the at least one seal element varies circumferentially about the axis between a first seal height at a first circumferential position and a second seal height at a second circumferential position.

20. The method of claim 19, wherein the first seal height is greater than the second seal height and is arranged to be located over a frontal region of the residual limb.

* * * * *